United States Patent [19]

Murib et al.

[11] Patent Number: 4,731,494

[45] Date of Patent: Mar. 15, 1988

[54] PROCESS FOR MAKING METHYL IODIDE FROM METHANE

[75] Inventors: Jawad H. Murib, Cincinnati; John H. Kahn, Wyoming, both of Ohio

[73] Assignee: National Distillers and Chemical Corporation, New York, N.Y.

[21] Appl. No.: 31,804

[22] Filed: Mar. 30, 1987

[51] Int. Cl.$^4$ ............................................. C07C 17/10
[52] U.S. Cl. ..................................................... 570/244
[58] Field of Search ......................................... 570/244

[56] References Cited

U.S. PATENT DOCUMENTS 2,407,828  9/1946  Gorin .................................. 570/244
3,080,435  3/1963  Nager .................................. 570/244

Primary Examiner—J. E. Evans
Attorney, Agent, or Firm—Kenneth D. Tremain

[57] ABSTRACT

A process for making methyl iodide is disclosed. In this process methane, and a source of oxygen are introduced into a molten salt, maintained at a temperature of at least about 500° C., said molten salt comprising an iodide of a metal selected from the group consisting of alkali metals, alkaline earth metals and mixtures thereof and a catalyst comprising at least one metal selected from the group consisting of a metal of Group IB and Group VIII of the Periodic Table of the Elements with the proviso that said methane and said source of oxygen do not contact each other.

27 Claims, No Drawings

PROCESS FOR MAKING METHYL IODIDE FROM METHANE

BACKGROUND OF THE DISCLOSURE

1. Field of the Invention

The present invention is directed to a process for making methyl iodide. More particularly, the instant invention is directed to a process for making methyl iodide by separately introducing methane and a source of oxygen into a molten salt comprising a metal iodide and a catalyst comprising a metal of Group IB or Group VIII of the Periodic Table of the Elements.

2. Background of the Prior Art

Methyl iodide is an important compound having many important uses. For example, methyl iodide is an excellent promoter in catalytic carbonylation reactions. In addition this compound is an effective methylating agent. It is also used in the synthesis of organometallic compounds used as intermediates in further organic synthesis. Methyl iodide, moreover, is a potential intermediate in the direct synthesis of hydrocarbons, such as ethylene, ethane and higher saturated and unsaturated aliphatic hydrocarbons. Those skilled in the art are aware that ethylene and higher alpha-olefins are building blocks in the synthesis of important commercial products such as plastic and rubber polymers.

Processes for the production of methyl iodide are known in the prior art. One such reference which teaches a process for converting methane to methyl iodide, however unsuccessfully, is provided in Broadbent et al., Trans. Faraday Soc., Vol. 67 (Pt. 10), 3030–3037 (1971). Broadbent et al. reported the formation of trace amounts of methyl iodide by the photochemical reaction of methane and iodine. The low yield of this reaction was attributed to the instability of the carbon-iodine bond.

U.S. Pat. No. 4,523,040, issued to Olah, describes a process for halogenating methane to produce methyl halides. This process involves the use of elemental chlorine or bromine in the presence of a solid acidic or metal catalyst.

Gorin et al., Ind. Eng. Chem., 40, 2128–2134 (1984) report the chlorination of methane with copper chloride-potassium chloride melts using a hydrogen chloride-air mixture in the absence of any basic salt to provide methyl chloride.

Other methods for producing methyl iodide are known, however, none of these conventional prior art processes involve a successful synthesis of methyl iodide from methane. Kirk and Othmer, "Encyclopedia of Chemical Technology," Third Edition, Vol. 13, 668, John Wiley and Sons, New York (1971) disclose that methyl iodide may be prepared by the reaction of methanol with phosphorus and iodine. In addition, methyl iodide may be produced by the reaction of dimethyl sulfate with an aqueous iodine slurry containing a reducing agent such as powdered iron or sodium bisulfite. In another conventional process methanol is reacted with hydriodic acid to produce methyl iodide. The reaction of potassium iodide with methyl p-toluenesulfate also forms methyl iodide. Other known reactions to produce this compound, as set forth in Kirk and Othmer, is the reaction of methylphenylether with iodine in the presence of aluminum. Finally, methyl iodide may be formed in high yield by the reaction of methanol with iodine and diborane. Although these processes result in the formation of methyl iodide none of these processes produce methyl iodide from methane in commercially significant yield.

SUMMARY OF THE INVENTION

A process has now been found wherein methyl iodide is produced in high selectivity in a commercially exploitable method utilizing abundantly available methane as the starting material.

In accordance with the present invention a process for making methyl iodide is disclosed. In this process methane and a source of oxygen are introduced into a molten salt comprising a metal iodide and a catalyst maintained at a temperature of at least about 500° C. If the molten salt is at a temperature of about 675° C. or above, steam must be additionally introduced into the melt. The metal of said metal iodide is selected from the group consisting of alkali metals, alkaline earth metals and mixtures thereof. The catalyst includes at least one metal selected from metals of Group IB and Group VIII of the Periodic Table of the Elements. The process is limited by the requirement that methane and the source of oxygen not contact each other.

DETAILED DESCRIPTION

The process of the present invention involves the introduction of methane and a source of oxygen into a molten salt, said salt comprising at least one metal iodide and a catalyst, maintained at a temperature of at least about 500° C. The metal of the metal iodide is selected from the group consisting of alkali metals, alkaline earth metals and mixtures thereof. The catalyst includes at least one metal selected from Group IB and Group VIII of the Periodic Table of the Elements. The process is limited by the requirement that the methane and the source of oxygen not contact each other.

The process of the present invention may be practiced in a continuous manner by feeding the methane and oxygen continuously into the respective legs of a reactor containing the molten salt while simultaneously feeding a source of iodide, preferably hydrogen iodide, in a continuous manner to either of the reactor legs to provide for the constant replacement of iodide which is depleted by the production and recovery of methyl iodide product.

The metal or metals utilized as the catalyst in the process of this invention may be present in elemental form, as a salt, preferably a halide and most preferably, an iodide or as an oxide. A mixture of two or more of these forms may also be employed. Of the Group IB metals, gold, silver and copper, silver and copper are preferred. Preferred metals within the metals of Group VIII are platinum, palladium and ruthenium. Still more preferably, the catalyst includes an element or compound selected from the group consisting of silver, silver iodide, copper, copper iodide, ruthenium, ruthenium oxide, ruthenium iodide and mixtures thereof. Of these, those catalysts containing ruthenium are particularly preferred. Thus, a catalyst selected from the group consisting of ruthenium, ruthenium oxide, ruthenium iodide and mixtures thereof is most preferred in the process of the present invention.

The metal or metals of Group IB and/or Group VIII utilized in the catalyst of the present invention may be unsupported or supported on an inert material. Of the supports within the contemplation of the preferred embodiment of the present invention, wherein a supported catalyst is used, those composed of alumina, titania, zirconia and mixtures thereof are preferred. Of these inert materials, alumina is most preferred.

The metal iodide component of the molten salt, which includes the above-described catalyst, includes at least one metal iodide, the metal of which is selected from the group consisting of alkali metals, alkaline earth metals and mixtures thereof. Preferably, the metal of the metal iodide is selected from the group consisting of sodium, lithium, calcium and mixtures thereof. Still more preferably, the metal of the metal iodide is an alkali metal selected from the group consisting of sodium and lithium. Yet more preferably, the metal iodide is lithium iodide.

As stated above, the molten salt into which methane and a source of oxygen are introduced is maintained at a temperature of at least about 500° C. Thus, the process of the present invention is conducted at or above atmospheric pressure and a temperature of at least 500° C. That is, the temperature at which the process of the present invention occurs is identical with the temperature of the molten salt. Preferably, the temperature of the molten salt, and hence the temperature of the process of the present invention to produce methyl iodide, is in the range of between about 500° C. and below about 675° C.

In a preferred embodiment the mixture into which methane and a source of oxygen are introduced includes at least one metal hydroxide. The metal of the metal hydroxide is selected from the group consisting of alkali metals, alkaline earth metals and mixtures thereof. Preferably, the metal hydroxide is a hydroxide of a metal selected from the group consisting of sodium, potassium and lithium and mixtures thereof. Still more preferably, the metal hydroxide is lithium hydroxide. It is especially preferred that when a metal hydroxide is employed the metal of the metal hydroxide be the same as the metal of the metal iodide.

In the preferred embodiment wherein a metal hydroxide is utilized the molar ratio of metal iodide to metal hydroxide is usually in the range of about 5:1 and about 80:1. More preferably, this molar ratio of metal iodide to metal hydroxide is in the range of between about 10:1 and about 20:1.

A major problem encountered in the processes involving methane and a source of oxygen, which is usually air or oxygen, as reactants is the hazard of explosion. Thus, it is important to maintain the ratio of methane to oxygen in the reactor outside the explosive range. However, the reaction of methane and oxygen, even when present in a ratio outside the explosive range, produces carbon oxides which decrease the yield of methyl iodide.

It is thus an aspect of the present invention to eliminate or minimize this undesirable side reaction by separating the source of oxygen from methane in the reactor to insure that these gases do not come in contact with each other. The process of the present invention is therefore designed to optimize the yield of methyl iodide while operating under safe reaction conditions. To effectuate this result the process is preferentially carried out in a molten reaction medium which is continuously circulated between two separate reaction zones of a "loop" reactor, such as that described in copending application, U.S. Ser. No. 07/031,828 filed 3/30/87.

In a preferred embodiment of the process of the present invention to produce methyl iodide, the oxygen feed is diluted with another gas. Among the diluent gases within the contemplation of the process of the present invention are steam, nitrogen, carbon dioxide, gases of Group VIII A of the Periodic Table, such as helium, neon and argon, mixtures thereof and the like. Of these diluent gases, steam or nitrogen is preferred for use in the process of this invention at temperatures below about 675° C. At temperatures of or above about 675° C. one specific diluent gas becomes essential. At reaction temperatures equal to or above about 675° C., steam must be introduced into the melt along with methane and a source of oxygen. Although the mechanism is not completely understood, at temperatures above about 675° C., the absence of steam results in the formation of hydrocarbons of two or more carbon atoms instead of methyl iodide. Thus, it is essential that steam be supplied in the process of the present invention when conducted at these recited high temperatures.

It is emphasized that while steam is used interchangeably with the other diluent gases at temperatures at or below about 675° C., at temperatures above about 675° C. the use of other diluent gases do not suffice. That is, the presence of a diluent gas other than steam does not result in the formation of methyl iodide. It is emphasized, however, that if another diluent gas is supplied along with steam, methyl iodide is synthesized.

In a particularly preferred embodiment of the present invention, methane, oxygen, steam and hydrogen iodide are continuously fed into a molten salt containing lithium iodide and lithium hydroxide and a ruthenium-containing catalyst, said melt maintained at a temperature in the range of between about 500° C. and about 750° C. wherein the methane and the oxygen are prevented from contacting each other.

In another preferred embodiment of the process of the present invention a source of iodide is introduced into the melt. Whereas, the source of oxygen and the methane are separately introduced into the molten salt, to insure against contact between the two gas streams, there is no limitation, in the preferred embodiment wherein a source of iodide is employed, regarding the introduction of the source of iodide. That is, the source of iodide may be introduced separately, with the source of oxygen, with the methane or with both the source of oxygen and methane.

The employment of a source of iodide is particularly desirable in those embodiments of the present invention wherein continuous operation is sought. Obviously, the iodide of the original molten iodide salt is depleted with time in that the iodide constituent supplies the iodine atoms for the methyl iodide product. Thus, a continuing source of iodide is essential to maintain the reaction. As such, the supply of a source of iodide represents a preferred embodiment of the process of the present invention.

The following examples are given to illustrate the scope of the present invention. Since these examples are provided for illustrative purposes only, the invention should not be limited thereto.

EXAMPLE 1

A loop reactor was constructed of two vertical 316 stainless steel pipes (1.6 cm ID×30 cm length) connected by an upper and a lower horizontal conduit. The reactor was charged with a powdered mixture of 225 g. lithium iodide; 5 g. lithium hydroxide; and 2 g. of 5 percent ruthenium on alumina. The powdered charge was added in increments and melted down at 700° C. This resulted in a liquid level above the upper conduit of the reactor. Methane gas was bubbled into the melt through one of the legs of the reactor at a rate of 120 cc/min. A gaseous mixture of 30 mole percent oxygen and 70 mole percent steam was bubbled into the other leg of the reactor at a rate of 90 cc/min.

The methane effluent from the reactor was cooled to room temperature to condense water vapor. The non-condensable gas was analyzed by gas chromatography and mass spectometry. The analysis showed that the gas consisted of 23.7% methyl iodide, 1.25% carbon dioxide and 75% methane, indicating that methyl iodide was produced in 95% selectivity with a 25% methane conversion per pass.

Examination of the reactor at the end of the experiment showed that the melt level had decreased below the upper conduit thereby permitting mixing of methane and oxygen which led to the observed combustion.

EXAMPLE 2

Example 1 was repeated except that the level of molten salt was kept above the upper conduit by adding the required amount of lithium iodide to prevent possible mixing of methane and oxygen feed gases. Analysis of the methane stream demonstrated formation of methyl iodide at 30% methane conversion per pass without detection of carbon dioxide. In addition, analysis of the salt disclosed the absence of elemental carbon or carbonates.

EXAMPLE 3

Example 2 was repeated in so far as the molten salt and its temperature (700° C.) were identical. However, the gases introduced into the melt were changed. Instead of the oxygen of Example 2, air, fed at a rate of 120 cc/min, was employed. Furthermore, steam, introduced into the melt in Example 2 with oxygen, was added to the molten salt with methane in a 53 mol % methane and 47 mole % steam mixture at a rate of 75 cc/min.

Analysis of the methane effluent evidenced the presence of methyl iodide.

EXAMPLE 4

Example 1 was repeated except that hydrogen iodide was fed continuously into the reactor instead of make-up lithium iodide. Methane was bubbled continuously into the melt which, like Example 1, was maintained at a temperature of 700° C., through one leg of the reactor at a rate of 44 cc/min. An aqueous solution of 11.4 weight % hydriodic acid was metered via a syringe pump into the other leg at a rate of 3 ml./hr., vaporized, wherein steam was formed, and fed into the melt together with a gaseous mixture of 10 cc/min. of oxygen and 22 cc/min. of nitrogen. Agitation and rotation of the melt was provided with a multi-blade propeller to effectuate a countercurrent flow of the melt with respect to the methane.

Analysis of the methane effluent showed that 6% of the methane was converted with selectivities of 59% methyl iodide, 12% ethylene and 29% carbon dioxide.

The formation of carbon dioxide is attributed to methane combustion resulting from oxygen being entrained in the fast moving melt through the upper conduit.

EXAMPLE 5

The loop reactor of Example 1, in this case equipped with a multi-blade propeller, was charged with a powdered mixture of 366 g. lithium iodide, 7.7 g. lithium hydroxide, 38 g. lithium sulfate, and 5.4 g. of ruthenium iodide. The powdered charge was added in increments and melted down at 575° C. Methane gas was bubbled into the melt through one of the legs of the reactor at a rate of 42 cc/min. A gaseous mixture of 30.4 mole percent oxygen and 69.6 mole percent nitrogen was bubbled into the melt through the other leg of the reactor at a rate of 34.5 cc/min.

Analysis of the methane effluent by gas chromatography showed that 1.5% of the methane was converted with 85% selectivity to methyl iodide and 15% selectivity to carbon dioxide.

EXAMPLES 6 to 9

The procedure of Example 5 was followed in each of Examples 6–9 except for temperature. The results of these examples are summarized in Table I. Table I includes the temperature of the melt, that is, the temperature of reaction. In addition, conversion of methane, in percent, and percent selectivity of the products is set forth in Table I. These results were obtained by gas chromatography.

The results of Table I establish that at 675° C. no methyl iodide is produced due to the absence of steam.

TABLE I
EFFECT OF TEMPERATURE ON CONVERSION OF METHANE TO METHYL IODIDE

| Example No. | Temp., °C. | % Conversion of Methane | % Selectivities to $CH_3I$ | $C_2$ Hydrocarbons | $CO_2$ |
|---|---|---|---|---|---|
| 5 | 575 | 1.5 | 85 | 0 | 15 |
| 6 | 600 | 1.8 | 77 | 4 | 19 |
| 7 | 625 | 2.0 | 49 | 28 | 23 |
| 8 | 650 | 1.8 | 30 | 41 | 29 |
| 9 | 675 | 2.4 | 0 | 85 | 15 |

EXAMPLE 10

A stainless steel reactor (2.2 cm ID × 10 cm length) was provided with a thermocouple at its base, a dip tube (0.4 cm ID × 0.6 cm OD) and a gas outlet at its top. To the molten salt at a temperature of 557° C., disposed in this reactor, was fed a mixed feed of 57 mole % methane, 14 mole % oxygen and 29 mole % steam at the rate of 140 cc/min. The molten salt contained 19 g. of lithium iodide and 33.4 g of silver iodide.

Analysis of the reactor effluent evidenced the presence of methyl iodide.

It is emphasized that this embodiment is supplied to exemplify the use of silver iodide as a catalyst within the scope of the present invention. Obviously, this embodiment is outside the preferred scope of the invention in that the methane and oxygen gas streams were not segregated.

COMPARATIVE EXAMPLE 1

The reactor of Example 10 was charged with 80 g. of lithium iodide, 2.6 g. of lithium hydroxide and 1 g. of 5% $Ru/AL_2O_3$ as catalyst. The charge was added and melted down at a temperature of 700° C. A mixed gaseous feed of 50 mole % methane, 12 mole % oxygen and 38 mole % steam was bubbled into the molten salt at a rate of 96 cc/min.

Analysis of the reactor effluent showed 5.4% of the methane was converted with selectivities of 20% methyl iodide and 80% carbon dioxide.

Comparative Example 1 is provided to emphasize the distinction between it and Example 1. Whereas the loop reactor of Example 1 insured against contact between the oxygen and methane gas streams, the reactor of the present comparative example did not. Thus, contact between oxygen and methane markedly reduced the selectivity to methyl iodide.

COMPARATIVE EXAMPLE 2

Two hundred twenty five (225) g. of lithium iodide was charged into the loop reactor of Example 1 along with 5 g. of lithium hydroxide. The iodides were heated to 652° C. at which point methane was bubbled into one leg of the reactor at the rate of 40 cc./min. and a gaseous mixture of 28.5 mole % oxygen and 71.5 mole % steam was bubbled into the other leg of the reactor at a rate of 35 cc./min.

Analysis of the methane effluent evidenced a conversion of 0.7% of the methane feed to carbon dioxide and water.

This unsuccessful run is ascribed to the absence of a catalyst within the contemplation of the present invention.

COMPARATIVE EXAMPLE 3

In a loop reactor, a mixed vapor of methane and iodine was bubbled into molten lithium iodide containing $Ru/Al_2O_3$ in an attempt to iodinate methane. Thus, methane was passed at a rate of 30 cc/min through a preheater containing iodine held at 110° C. The mixed vapor was fed into molten lithium iodide (236 g.) containing 4 g. of 5% $Ru/Al_2O_3$, heated at 600° C.

Analysis of the reactor effluent indicated the absence of methyl iodide demonstrating that methane and iodine do not react to form methyl iodide under these conditions.

COMPARATIVE EXAMPLE 4

Comparative Example 3 was repeated except that the molten salt also contained lithium hydroxide.

Analysis of the reactor effluent disclosed that methyl iodide was not formed.

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A process for making methyl iodide from methane comprising introducing methane and a source of oxygen into a molten salt, maintained at a temperature in the range of between about 500° C. and below about 675° C., comprising an iodide of a metal selected from the group consisting of alkali metals, alkaline earth metals and mixtures thereof and a catalyst comprising at least one metal selected from the group consisting of metals of Group IB and Group VIII of the Periodic Table of the Elements with the proviso that said methane and said source of oxygen not contact each other.

2. A process in accordance with claim 1 wherein the metal of said metal iodide is selected from the group consisting of sodium, lithium, calcium and mixtures thereof.

3. A process in accordance with claim 2 including introducing a source of iodide into said molten salt.

4. A process in accordance with claim 3 wherein said source of iodide is hydrogen iodide.

5. A process in accordance with claim 2 wherein said molten salt comprises a hydroxide of a metal selected from the group consisting of alkali metals, alkaline earth metals and mixtures thereof.

6. A process in accordance with claim 5 wherein the molar ratio of said metal iodide to said metal hydroxide is in the range of between about 5:1 and about 80:1.

7. A process in accordance with claim 6 wherein said molar ratio of said metal iodide to said metal hydroxide is in the range of between about 10:1 and about 20:1.

8. A process in accordance with claim 2 including introducing a diluent gas into said molten salt.

9. A process in accordance with claim 8 wherein said diluent gas is selected from the group consisting of steam, nitrogen, carbon dioxide, gases of Group VIIIA of the Periodic Table of the Elements and mixtures thereof.

10. A process in accordance with claim 9 wherein said diluent gas is selected from the group consisting of steam and nitrogen 11. A process in accordance with claim 2 wherein said source of oxygen is a gas selected from the group consisting of oxygen and air.

12. A process in accordance with claim 2 wherein said metal of said metal iodide is selected from the group consisting of sodium, lithium and mixtures thereof.

13. A process in accordance with claim 5 wherein said metal of said metal iodide and said metal of said metal hydroxide is lithium.

14. A process in accordance with claim 2 wherein said catalyst includes at least one metal selected from the group consisting of silver, copper, platinum, palladium and ruthenium.

15. A process in accordance with claim 14 wherein said catalyst is selected from the group consisting of ruthenium, ruthenium oxide, ruthenium iodide and mixtures thereof 16. A process in accordance with claim 2 wherein said catalyst is supported on an inert material selected from the group consisting of alumina, titania, zirconia and mixtures thereof.

17. A process in accordance with claim 2 wherein said catalyst is selected from the group consisting of ruthenium iodide and ruthenium on alumina.

18. A process for making methyl iodide from methane comprising introducing methane, a source of oxygen, and steam into a molten salt, maintained at a temperature at or above about 675° C., said molten salt comprising an iodide of a metal selected from the group consisting of alkali metals, alkaline earth metals and mixtures thereof and a catalyst comprising at least one metal selected from the group consisting of metals of Group IB and Group VIII of the Periodic Table of the Elements with the proviso that said methane and said source of oxygen do not contact each other.

19. A process in accordance with claim 18 including introducing a source of iodide into said molten salt.

20. A process in accordance with claim 19 wherein said source of iodide is hydrogen iodide.

21. A process in accordance with claim 18 wherein said molten salt comprises a hydroxide of a metal selected from the group consisting of alkali metals, alkaline earth metals and mixtures thereof.

22. A process in accordance with claim 21 wherein said metal iodide is lithium iodide and said metal hydroxide is lithium iodide.

23. A process in accordance with claim 22 wherein said lithium iodide and said lithium hydroxide are present in a ratio of lithium iodide to lithium hydroxide in the range of between about 5:1 and 80:1.

24. A process in accordance with claim 23 wherein said ratio of said lithium iodide to lithium hydroxide is in the range of between about 10:1 and 20:1.

25. A process in accordance with claim 18 wherein said source of oxygen is a gas selected from the group consisting of oxygen and air.

26. A process in accordance with claim 18 wherein said catalyst includes at least one metal selected from the group consisting of silver, copper, platinum, palladium and ruthenium.

27. A process for making methyl iodide from methane comprising introducing methane, oxygen, steam and hydrogen iodide into a molten salt, maintained at a temperature in the range of between about 500° C. and about 750° C., said molten salt comprising lithium iodide and lithium hydroxide and a ruthenium-containing catalyst with the proviso that said methane and said oxygen do not contact each other.

* * * * *